United States Patent [19]

Kunselman et al.

[11] Patent Number: 5,436,723
[45] Date of Patent: Jul. 25, 1995

[54] SPECTROSCOPIC ANALYSIS

[75] Inventors: Garry C. Kunselman, Stow; Richard L. Crawford, Attleborough, both of Mass.

[73] Assignee: Thermo Jarrell Ash Corporation, Franklin, Mass.

[21] Appl. No.: 27,209

[22] Filed: Mar. 5, 1993

[51] Int. Cl.⁶ .............................. G01J 3/36; G01J 3/30
[52] U.S. Cl. .................................. 356/307; 356/316; 356/328
[58] Field of Search ............... 356/300, 311, 316, 307, 356/326, 328

[56] References Cited

U.S. PATENT DOCUMENTS

| | | | |
|---|---|---|---|
| 3,508,813 | 4/1970 | Smith, Jr. et al. | 350/275 |
| 3,532,429 | 10/1970 | Hughes et al. | 356/95 |
| 4,469,441 | 9/1984 | Bernier et al. | 356/316 |
| 4,575,241 | 3/1986 | Demers et al. | 356/316 |
| 4,930,892 | 6/1990 | Hadbawnik et al. | 356/328 |
| 4,973,159 | 11/1990 | Sohma et al. | 356/316 |
| 5,141,314 | 8/1992 | Belmore et al. | 356/313 |

FOREIGN PATENT DOCUMENTS

| | | |
|---|---|---|
| 0362562 | 9/1989 | European Pat. Off. |
| 0558216A1 | 9/1993 | European Pat. Off. |
| 57-069220 | 4/1982 | Japan |

*Primary Examiner*—Rolf Hille
*Attorney, Agent, or Firm*—Fish & Richardson

[57] ABSTRACT

A spectroanalytical system with radiation dispersing apparatus for dispersing radiation into a spectrum for concurrent application to an array of exit ports; sample excitation apparatus for exciting sample material to be analyzed to spectroemissive levels for generating a beam of radiation for dispersion by the dispersing structure; the exit port array including a corresponding array of detectors including a first detector positioned adjacent a first exit port positioned to sense first order radiation from an element of interest and a second detector positioned adjacent a second exit port to sense second order radiation from the same element of interest; and processing apparatus for responding to outputs of the first and second detectors to provide a compensated output as a function of the quantity of the element of interest in the sample material.

20 Claims, 2 Drawing Sheets

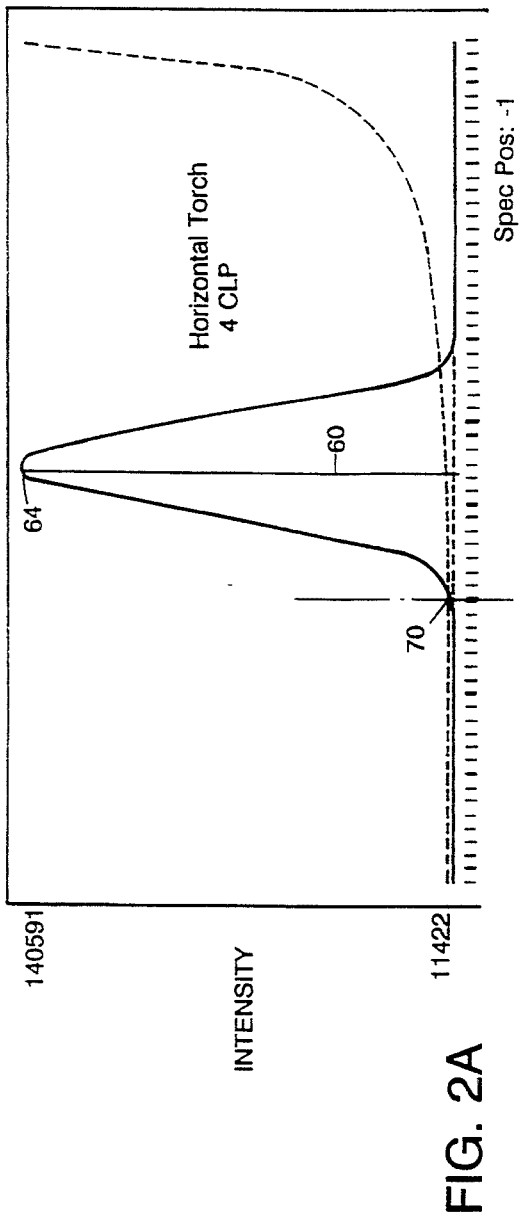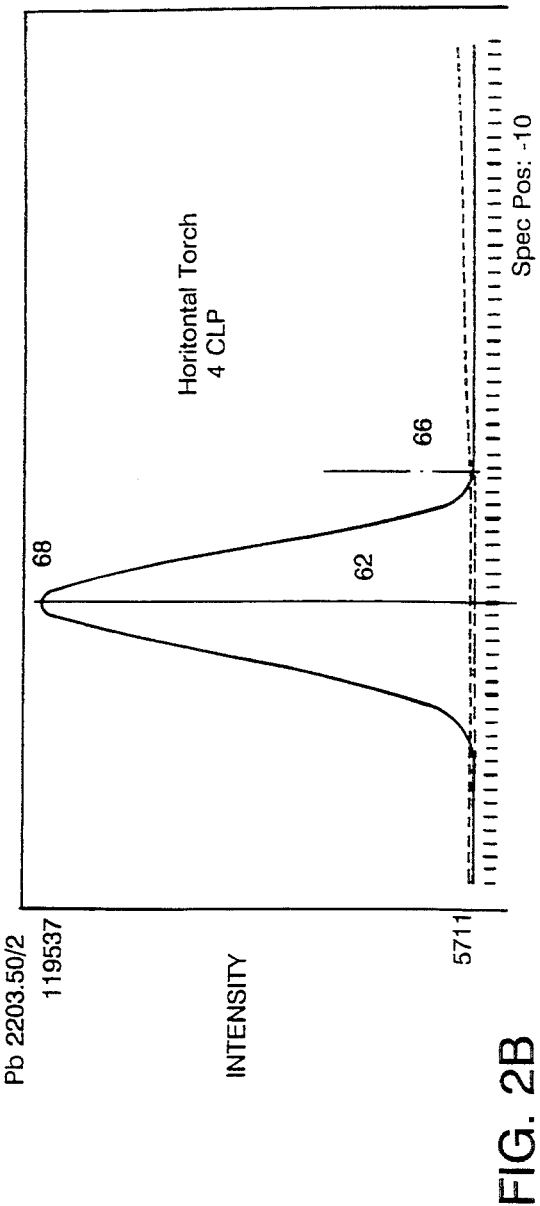

SPECTROSCOPIC ANALYSIS

This invention relates to spectroscopic analysis and more particularly to spectroanalytical processes and systems of the polychromator type.

BACKGROUND OF THE INVENTION

In spectroanalytical systems using emission sources, material to be analyzed is introduced into an analytical region and excited to spectroemissive levels sufficient to emit detectable radiation characteristic of elements in the sample. The resulting emitted radiation typically is dispersed and analyzed spectroscopically to quantitatively determine elemental compositions of sample materials. An example of such analyses is the contract lab program (CLP) in which sample materials are analyzed for the toxic elements, arsenic, thallium, selenium and lead. Prior analytical systems for measurements of this CLP type have employed an atomic absorption graphite furnace with a hollow cathode lamp for each element of interest. An object of the invention is to provide a polychromator with improved detection limits suitable for analyses of the CLP type.

SUMMARY OF THE INVENTION

In accordance with one aspect of the invention, there is provided a spectroanalytical system with radiation dispersing apparatus for dispersing radiation into a spectrum for concurrent application to an array of exit ports; sample excitation apparatus for exciting sample material to be analyzed to spectroemissive levels for generating a beam of radiation for dispersion by the dispersing structure; the exit port array including a corresponding array of detectors including a first detector positioned adjacent a first exit port positioned to sense first order radiation from an element of interest and a second detector positioned adjacent a second exit port to concurrently sense second order radiation from the same element of interest; and processing apparatus for responding to outputs of the first and second detectors to provide a compensated output as a function of the quantity of the element of interest in the sample material.

In accordance with another aspect, there is provided a polychromator system with housing structure, entrance aperture defining structure in the housing structure for passing a beam of radiation from sample material excited to spectroemissive levels, dispersing structure in the housing structure for dispersing radiation in the beam into a spectrum, structure in the housing structure defining a plurality of exit apertures, first order detector structure associated with a first exit aperture structure, second order detector structure associated with a second exit aperture structure, and selecting structure operable at a first condition maximizing the amplitude of said first order detector structure and a second condition maximizing the amplitude of said second order detector structure. Signal processing apparatus is coupled to the first and second detector structures for processing first and second order measurements to provide a compensated value of an element of interest in the sample material.

In preferred embodiments, astigmatism correcting optical structure is provided between the source and the dispersing structure, that structure including a curved entrance slit and a cylindrical lens in a particular embodiment.

In a particular embodiment, the selecting structure includes spectrum shifter apparatus disposed between the entrance aperture defining structure and the dispersing structure for shifting the beam relative to the dispersing structure to shift the spectrum between a first order maximum and a second order maximum for a particular element; the dispersing structure is a reflection grating that has at least one thousand lines per millimeter; and the sample excitation source is an induction coupled plasma disposed along a path coincident with the entrance beam axis. Included in the input optics is circular aperture structure for passing radiation from the central portion of the plasma and blocking radiation from the circumferential portions. The polychromator system is of the Paschen Runge type, the entrance aperture structure has a width of about twenty-five micrometers and a height of about twenty millimeters, each exit aperture includes a slit having a height of about four millimeters, and the entrance and exit apertures and the reflection grating are disposed on a Rowland circle of at least about 0.5 meter diameter. The system is adapted to analyze sample material for several different elements such as arsenic, thallium, selenium and lead concurrently and provides detection limits in the order of 3–5 parts per billion.

In accordance with another aspect of the invention, there is provided a spectroanalytical process that includes the steps of generating a beam of radiation from sample material excited to spectroemissive levels, dispersing radiation in the beam into a spectrum, concurrently sensing first order radiation and second order radiation corresponding to a particular element of interest in the sample material, the output amplitude of one order radiation being maximized while the other order radiation concurrently provides a background level output amplitude, and processing the concurrently sensed first and second order radiations to provide a background compensated value of the particular element of interest in the sample material.

In a particular process, the first and second order maximum radiations are offset from one another by a factor of about 0.1 Angstrom; the process determines the difference between first and second measurements of a particular element of interest at a first order detector and converts that intensity to concentration units ($A_x$); determines the difference between second and first outputs at a second order detector to provide a second concentration unit value ($B_x$); and applies BEC (background equivalency concentration) weighing factors a and b to provide compensation according to the equation $(bA_x + aB_x)/(a+b)$; and the process is adapted to analyze sample material concurrently for arsenic, thallium, selenium and lead.

BRIEF DESCRIPTION OF DRAWINGS

Other features and advantages of the invention will be seen as the following description of a particular embodiment progresses, in conjunction with the drawings, in which:

FIGS. 2a and 2b are plots of data obtained with the system shown in FIG. 1.

DESCRIPTION OF PARTICULAR EMBODIMENT

Figure 1:
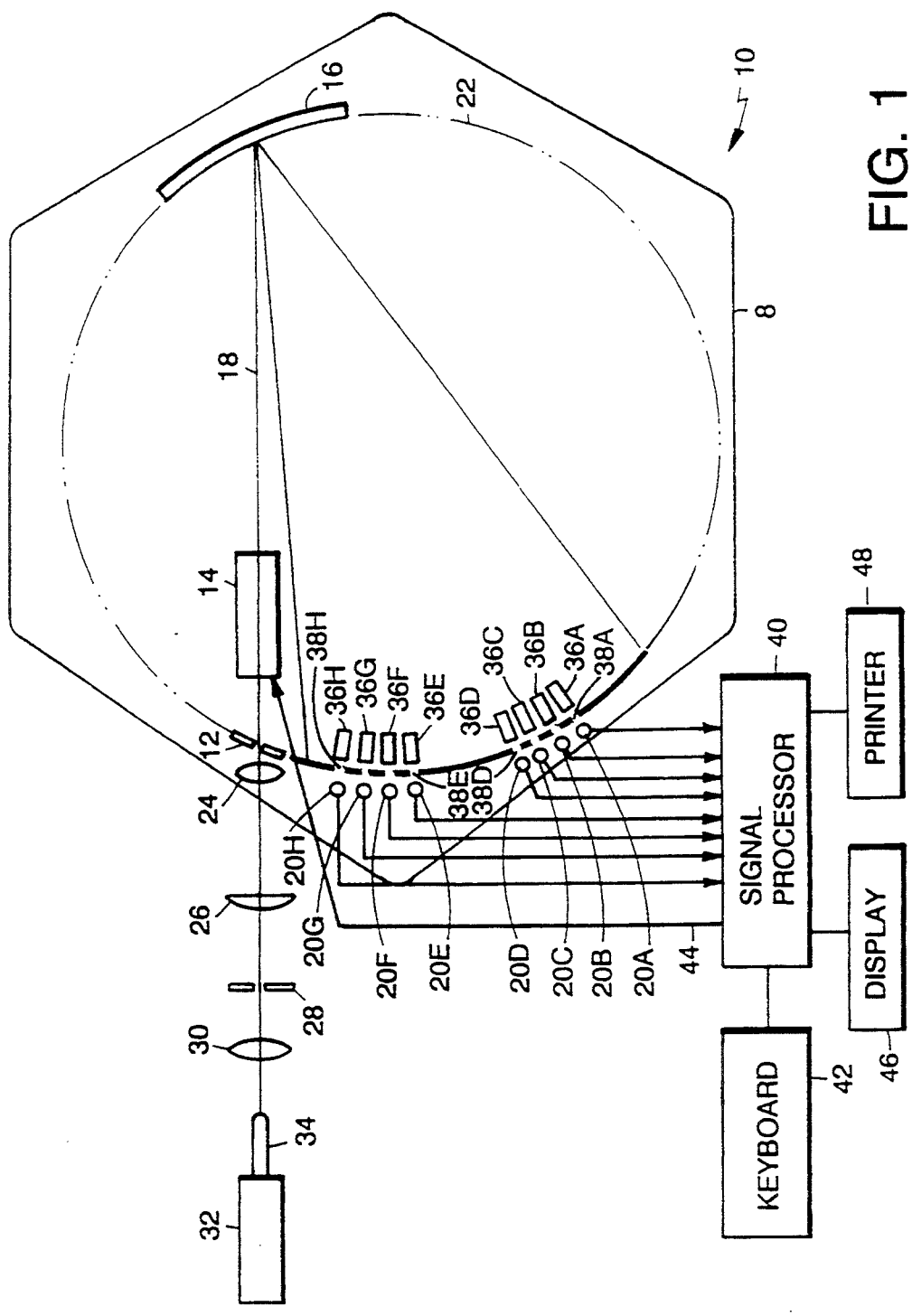
FIG. 1 is a diagram of a spectroanalytical system in accordance with the invention.

With reference to FIG. 1, the spectroanalytical system there diagrammatically illustrated includes polychromator 10 with housing structure, 8 entrance slit structure 12, spectrum shifter 14, and reflection grating 16 for dispersing incident radiation on beam axis 18 into a spectrum for sensing by a selected group of photomultiplier tube sensors 20A–H disposed along Rowland circle 22 that has a radius of curvature of 0.75 meter. Disposed immediately in front of entrance slit 12 is spherical focusing lens 24; and spaced along beam axis 18 are UV cylindrical lens 26; aperture 28; UV achromat lens 30; and induction coupled plasma source 32 disposed so that the plasma 34 is "end on" and aligned with beam axis 18. The plasma (ICP) 34 is of toroidal configuration with a central portion of about 2–3 millimeter diameter. Aperture 28 has a diameter of about two millimeters and passes radiation from the central portion of the plasma; cylindrical lens 26 has a focal length of about sixty millimeters; and entrance slit 12 has a width of about twenty-five micrometers and a height of about eighteen millimeters and is curved (in the vertical direction—perpendicular to the axis of lens 26) at a radius of about one half meter. Grating 16 is a spherical holographic grating with dimensions of about sixty millimeters by seventy millimeters and 2,400 lines per millimeter. The combination of optical elements and the curved entrance slit provides correction for astigmatism and the reduced aberrations enable use of larger grating area.

Disposed between grating 16 and each sensor 20 are a refractor plate mechanism 36 and an exit slit structure 38 which defines a slit of about twenty five micrometers width and about four millimeters height. The input optics image exit slits 38 at input aperture 28. Included in the detector array are first order arsenic detector 20A at 1890 Angstroms and second order arsenic detector 20E at about 3780.1 Angstroms (about 0.1 Angstrom offset); first order thallium detector 20B at 1908 Å and second order thallium detector 20F at about 3816.1 Å; detector 20C at 1960 Å and second order selenium detector 20G at about 3919.9 Å; and first order lead detector 20D at 2203 Å and second order lead detector 20H at about 4405.9 Å. Detectors 20 are connected to signal processor 40 which responds to input commands from controller 42 which typically includes a keyboard, produces control signals on line 44 to cause spectrum shifter 14 to select desired first or second order wavelength peaks, and processes information generated from photomultiplier tubes 20A–H for application to output devices such as display 46 and printer 48.

In a processing sequence, the sample material to be analyzed is inputted into ICP source and excited to spectroemissive levels. Processor 40 first positions spectrum shifter 14 at a first order peak position and concurrently responds to outputs of first and second order detectors of the elements of interest at a first interval of time, where the spectrum shifter 14 is positioned to maximize the outputs of the first order detectors; and, then at a second period of time where the spectrum shifter 14 is positioned to maximize outputs of the second order detectors, and again responds to the outputs of the two sets of detectors. Processor 40 then determines the difference between the first and second measurements of a particular element of interest at the first order detector and converts that intensity to concentration units ($A_x$); similarly, the difference between the second and first outputs at the second order detector to provide second concentration unit values ($B_x$); and applies BEC (background equivalency concentration) weighting factors a and b to provide compensation according to the equation $(bA_x + aB_x)/(a+b)$ (Equation 1). In typical measurements for particular elements of interest, BEC weighting factor coefficients a and b are as follows:

|  | a | b |
|---|---|---|
| Arsenic | 2 | 1 |
| Thallium | 1 | 1 |
| Selenium | 2 | 1 |
| Lead | 2 | 1 |

Shown in FIG. 2 are the outputs of the first order lead sensor 20D (FIG. 2a) and the output of the second order sensor lead 20H (FIG. 2b). The first order peak measurement for the 20D detector is at about 2203.5 Å wavelength (line 60) and for the second order peak measurement is at about 4406.9 Angstroms (an offset of about 0.1 Angstrom) (line 62). Measurements are concurrently recorded at the first order peak 64 and the second order background (point 66); the spectrum shifter 14 then is stepped nine steps to shift the dispersed spectrum about 0.15 Angstrom; and second measurements are concurrently recorded at second order peak 68 and first order background point 70. The background measurement 70 at the first order peak wavelength is subtracted from the first order peak measurement 64 to obtain the $A_x$ value; and the second order background measurement at point 66 is subtracted from the second order peak measurement 68 to obtain the $B_x$ value. The two compensated values are then further processed according to equation (1) and the results are displayed at output device 48. With this system, lead in the sample can be measured with detection limits of about two parts per billion in particular samples. Other elements are also measured with similar detection limits.

While a particular embodiment of the invention has been shown and described, various modifications will be apparent to those skilled in the art, and therefore, it is not intended that the invention be limited to the disclosed embodiment, or to details thereof, and departures may be made therefrom within the spirit and scope of the invention.

What is claimed is:

1. A polychromator system comprising
housing structure,
sample excitation structure,
entrance aperture defining structure in said housing structure for passing a beam of radiation from sample material excited to spectroemissive levels by said sample excitation structure,
dispersing structure in said housing structure for dispersing radiation in said beam into a spectrum,
structure in said housing structure defining a plurality of exit apertures,
first order detector structure associated with a first said exit aperture structure, second order detector structure associated with a second said exit aperture structure,
selecting structure having a first condition maximizing the amplitude of the output of said first order detector structure and a second condition maximizing the amplitude of the output of said second order detector structure, and
signal processing apparatus coupled to said first and second detector structures for processing the differences between first and second order outputs of said detector structures to provide a compensated value of an element of interest in said sample material.

2. The system of claim 1 and further including astigmatism correcting optical structure between said source and said dispersing structure.

3. The system of claim 1 wherein said entrance aperture defining structure includes astigmatism correcting optical structure that defines a slit curved along a path perpendicular to the plane defined by said entrance and exit aperture structures and said dispersing structure for providing astigmatism correction.

4. The system of claim 1 wherein said selecting structure includes spectrum shifter apparatus disposed between said entrance aperture defining structure and said dispersing structure for shifting said beam relative to said dispersing structure to shift said spectrum between a first order maximum and a second order maximum for a particular element.

5. The system of claim 1 wherein said sample excitation structure is an induction coupled plasma source disposed along a path coincident with said entrance axis.

6. The system of claim 1 wherein said system is of the Paschen-Runge type, said entrance aperture defining structure has a width of about twenty-five micrometers and a height of about twenty millimeters, and each said exit aperture includes a slit having a height of about four millimeters.

7. The system of claim 1 wherein said entrance and exit apertures and said dispersing structure are disposed on a Rowland circle of at least about 0.5 meter diameter.

8. The system of claim 1 wherein said dispersing structure is a reflection grating that has at least one thousand lines per millimeter.

9. The system of claim 1 wherein said system is adapted to analyze said sample material for arsenic, thallium, selenium and lead.

10. A polychromator system comprising
housing structure,
sample excitation structure,
entrance aperture defining structure in said housing structure for passing a beam of radiation from sample material excited to spectroemissive levels by said sample excitation structure,
dispersing structure in said housing structure for dispersing radiation in said beam into a spectrum,
structure in said housing structure defining a plurality of exit apertures,
first order detector structure associated with a first said exit aperture structure, second order detector structure associated with a second said exit aperture structure,
structure for maximizing the output amplitude of one of said detector structures in response to said beam of radiation from a particular sample material while concurrently providing a background level output amplitude of the other of said detector structures, and
signal processing apparatus coupled to said first and second order detector structures responsive to concurrent outputs of said first and second order detector structures to provide a background compensated value of an element of interest in said sample material.

11. The system of claim 10 wherein said entrance aperture defining structure defines a slit that is curved at a radius in the range of about 0.1 and 1.0 meter along a path perpendicular to the plane defined by said entrance and exit aperture structures and said dispersing structure for providing astigmatism correction.

12. The system of claim 10 wherein said sample excitation structure is an induction coupled plasma source disposed along a path coincident with said radiation beam and further including circular aperture structure between said plasma source and said entrance aperture defining structure for passing a central portion of said plasma and obstructing circumferential portions of said plasma.

13. The system of claim 12 and further including spectrum shifter apparatus disposed between said entrance aperture defining structure and said dispersing structure for shifting said beam relative to said dispersing structure to shift said spectrum between a first order maximum and a second order maximum for a particular element.

14. The system of claim 13 and further including astigmatism correcting cylindrical lens structure between said source and said dispersing structure.

15. The system of claim 13 wherein said system is of the Paschen-Runge type, said entrance aperture defining structure has a width of about twenty-five micrometers and a height of about twenty millimeters, and each said exit aperture includes a slit having a height of about four millimeters.

16. The system of claim 15 wherein said system is adapted to analyze said sample material for arsenic, thallium, selenium and lead.

17. A spectroanalytical process comprising the steps of generating a beam of radiation from sample material excited to spectroemissive levels,
dispersing radiation in said beam into a spectrum,
concurrently sensing first order radiation and second order radiation corresponding to a particular element of interest in said sample material, the output amplitude of one of said order radiations being maximized while the other order radiation concurrently provides a background level output amplitude, and
processing said concurrently sensed first and second order radiations to provide a background compensated value of said particular element of interest in said sample material.

18. The process of claim 17 wherein said maximum first and second order radiations are offset from one another by a factor of about 0.1 Angstrom.

19. The process of claim 17 wherein said processing step determines the difference between the first and second measurements of a particular element of interest at a first order detector and converts that intensity to concentration units ($A_x$); determines the difference between the second and first outputs at a second order detector to provide a second concentration unit value ($B_x$); and applies BEC (background equivalency concentration) weighting factors a and b to provide compensation according to the equation $(bA_x+aB_x)/(a+b)$.

20. The process of claim 19 wherein said process is adapted to analyze said sample material concurrently for arsenic, thallium, selenium and lead.

* * * * *